US008219185B2

(12) United States Patent
Lin et al.

(10) Patent No.: US 8,219,185 B2
(45) Date of Patent: Jul. 10, 2012

(54) RAPID METHOD FOR ANALYZING BIO-SIGNAL INSTANTANEOUSLY BY PHASE SPACE COMPLEXITY DIFFERENCE AND ITS DEVICE

(75) Inventors: Chii-Wann Lin, Taipei (TW);
Tzn-Chien Hsiao, Shrlin Chiu (TW);
Chien-Sheng Liu, Taichung (TW)

(73) Assignee: National Taiwan University (TW)

( * ) Notice: Subject to any disclaimer, the term of this patent is extended or adjusted under 35 U.S.C. 154(b) by 263 days.

(21) Appl. No.: 12/702,344

(22) Filed: Feb. 9, 2010

(65) Prior Publication Data
US 2010/0179396 A1    Jul. 15, 2010

Related U.S. Application Data

(63) Continuation-in-part of application No. 11/967,745, filed on Dec. 31, 2007, now abandoned.

(30) Foreign Application Priority Data

Nov. 2, 2007 (TW) ................................ 96141581 A

(51) Int. Cl.
*A61B 5/04* (2006.01)
(52) U.S. Cl. ........................................................ 600/509
(58) Field of Classification Search ................... 600/509
See application file for complete search history.

(56) References Cited

U.S. PATENT DOCUMENTS

| 5,643,325 A | * | 7/1997 | Karagueuzian et al. | .......... 607/8 |
| 5,794,623 A | * | 8/1998 | Forbes | .......... 600/515 |
| 2009/0076402 A1 | * | 3/2009 | Hoium et al. | .......... 600/515 |

FOREIGN PATENT DOCUMENTS

WO    2004023995    3/2004

OTHER PUBLICATIONS

Office Action (Mail Date: Oct. 5, 2009) for U.S. Appl. No. 11/967,745, filed Dec. 31, 2007.

* cited by examiner

*Primary Examiner* — George Manuel
*Assistant Examiner* — Robert N Wieland
(74) *Attorney, Agent, or Firm* — Schmeiser, Olsen & Watts, LLP

(57) ABSTRACT

The present invention relates to a method for analyzing bio-signal instantaneously by Chaotic Phase Space Difference (CPSD) operation and its measure analyze device. This method includes time-delay procedure and rebuilt phase space matrix to calculate complexity of phase space matrix and diagnose the bio-signal. This method can also be used as an analyze method in portable device or 24 h ECG recorder which is a fast and convenient measure analyze device.

13 Claims, 15 Drawing Sheets

RAPID METHOD FOR ANALYZING BIO-SIGNAL INSTANTANEOUSLY BY PHASE SPACE COMPLEXITY DIFFERENCE AND ITS DEVICE

CROSS-REFERENCE TO RELATED APPLICATIONS

This application is a continuation-in-part patent application of U.S. application Ser. No. 11/967,745 filed on Dec. 31, 2007, the entire contents of which are hereby incorporated by reference for which priority is claimed under 35 U.S.C. §120.

TECHNICAL FIELD

The present invention relates to a rapid method and device for measuring, recording and analyzing bio-current signal of the human body, and particularly to a method and device for measuring, recording and analyzing bio-signal using Chaotic Phase Space Difference (CPSD) analysis method.

BACKGROUND OF THE INVENTION

The bio-signal could be used to evaluate and diagnose the important parameters for biological status, which employs the analysis on the bio-signal to be provided as the reference of clinical diagnosis. The bio-signal is characterized in having a periodically changing signal. The commonly used bio-signal includes the electrocardiogram (ECG or EKG, although both signals are well known in this field as the same signal, but for purpose of present invention, the electrocardiogram will be referred as ECG), Heart Sound or Respiration Signal, which could be used to evaluate the cardiovascular system and lung function respiration system. The basic principles are briefly described as follows.

As shown in FIG. 1, the heart structure could be divided as two portions, the atrium and the ventricle, in which the atrium portion is connected with the upper and lower chamber veins. When the right atrium is full of the blood returned by the veins, the sinoatrial node (101) on the right atrium will spontaneously generate the depolarized action potential. The current signal will be transmitted to the left atrium through the muscle cells of the atrium. Because the muscle cells of the heart is provided with the ion channels suitable for electrical connection, the signal transmission is very fast, so that the left and right atriums will almost simultaneously depolarized, and further generate the contraction of muscle fibers, and generate the mechanical energy power to extrude the blood into the ventricle. At this time, the depolarized current signal will be transmitted to the atrio-ventricular node (102) at the bottom of the right ventricle. Because the signal transmission speed of the atrio-ventricular node is slower, the ventricle will have enough time to complete the operation of depolarized contraction.

Next, the atrio-ventricular node will transmit the depolarized current signal to the entire left and right atriums through the Purkinje fibers (106), so the left and right ventricles are depolarized contraction simultaneously, and extrude the blood to the upper and lower chamber arteries, and accomplish a complete heart beat cycle. It could be noted that the heart employs the weak nerve current signal transmission to achieve the contraction and diastole action. Because the human body is a conductor, the current will conduct and flow all over the body through the human tissues. At this time, if attaching the conductible electrode patch on the body surface, it could employ the signal abscontraction circuit to record the current signal, and this signal is referred as the electrocardiogram (ECG or EKG) signal.

Generally in the ECG of so-called second leads body surface electrode record, the main signal composition is shown in FIG. 2A, which includes a P-wave representing the waveform signal measured and recorded on the body surface when the atrium is depolarized contraction, in which the measured and recorded is a QRS composite wave after about 0.15 seconds representing the depolarized contraction of the ventricle. At the same time, the ventricle will have the repolarized diastolic effect. But the repolarized signal strength of the ventricle is smaller than the depolarized signal strength, it could not be observed in ECG. The final T-wave represents the signal measured and recorded during repolarized diastole of the atrium. It could be found in the associated research, in various clinic diagnosis of diseases, the ECG will be appeared to present abnormal waveform or abnormal variation, such as ventricular hypertrophy, arrhythmia, myocardial infarction, coronary artery incompetence, and the like.

The heart sound signal is recorded with the sound given when the heart valve is closed. The most easily observed is the first heart sound (S1) and the second heart sound (S2), as shown in FIG. 2B. In the clinic, if the heart has the abnormal condition in the biological structure, besides of S1 and S2, there will be other murmur occurring. As shown in FIG. 2C, the signal occurred between S1 and S2 is the murmur, which is an important basis for determining heart disease.

Biologically, the speed of heart beat is controlled by various mechanisms, in which one of the important mechanisms is the respiration, and the speed of respiration will cause the variation of blood oxygen density, which will indirectly affect the heart rate. FIG. 2D shows the measurement result of the respiration signal.

In the method for analyzing bio-signal, the major domains have two portions: one is the analysis of frequency domain, which employs the fast Fourier Transform (FFT) to calculate the power spectrum of the bio-signal and observe the variance in the frequency domain. For example, in the analysis of heart rate variability (HRV) for calculating the ratio of band energy of LF (0.04~0.15 Hz) and HF (0.15~0.4 Hz), it is to observe the effect of the sympathetic nerve and the parasympathetic nerve to the heart rate variation; another one is to observe the waveform variance of the bio-signal, which is based on the analysis of Chaos Theory to understand the waveform distortion effect on the bio-signal caused by the disease, in which the commonly used analysis is the phase space matrix reconstruction. In the CPSD (Chaotic Phase Space Difference) algorithm, it employs the calculation of CPSD to generate the reference data for determining the bio-signal. For the application of ECG, it first could be used to calculate the heart rate, which has replaced the conventional R-R interval calculation method, and effectively solved the problem of threshold value selection in R-R interval calculation, and it could further easily determine the normal and abnormal ECG signal. In the application of heart sound, it could employ the CPSD algorithm to distinguish S1 and S2 to differentiate the murmur, and calculate the heart rate instantaneously. In the application of respiration signal, the CPSD algorithm could be used to calculate the variance of respiration rate.

In WO 2004/023995 published on Mar. 25th, 2004, it disclosed a device and method for measuring subcutaneous ECG waveform through the R-wave algorithm. The device is mainly used for implanted defibrillator or inserted loop recorder, and employs the interval difference between R-wave and R-wave to determine if arrhythmia has occurred and as the basis of recording and defibrillating. In the calculation of measurement method, employing the R-wave algorithm and the automatic threshold value regulation method to precisely abstract the R-wave message as the basis of calculation of interval difference between R-waves.

Although using the interval difference between R-waves as the measurement method for ECG has been disclosed in the content of the prior art, using the interval difference between R-waves as the ECG measurement method will be limited by the selection of the threshold, which could not easily and rapidly differentiate the difference between normal and abnormal ECG signals. In order to solve this problem, it is required an ECG analysis method for easily editing, fast processing speed, saving the storage space, and reducing consumed system resources.

U.S. Pat. No. 5,794,623 teaches using electrocardiogram (ECG) signals from a body to analyze the irregular intramyocardial Wenckebach activity (MWA) in the heart of a patient. This prior art discloses using a mechanism for measuring respiratory signals from the body and a processor electrically associated with the two mechanisms means for measuring the presence of intramyocardial Wenckebach activity of two or more phases. The Wenchebach basis function strengths is calculated by the processor to indicate the presence of voltage in the measured ECG signals caused by the repeating patterns of irregular intramyocardial Wenckebach activity via a relationship that describes the measured ECG signals as comprising Wenckebach input being additive to respiratory interference. This conventional method is suitable for calculate the interference and noise by analyzing the breathing signal of the patient and myocardial Wenckebach activity to classify ventricular fibrillation but is not appropriate for analyzing the periodical bio-signal by CPSD.

U.S. Pat. No. 5,643,325 discloses a method for detecting a hear disorder by using a phase-plan plot (PPP) of a patient electrocardiogram (ECG). The PPP's degree of deterministic chaos is measured by a processor, and the PPP result is analyzed by Lyapunov exponent or Poincare section method to indicate the risk of fibrillation and its actual onset where the risk is 100 percent. The prior art further teaches using a frequency-domain transform (such as an FFT) of a patient ECG. Nth derivative theorem is employed to use a plot of variable of ECG signals, such as voltage, and derivative value ($dV/dt$, $d^2 V/dt^2$) to construct a phase-plane plot (ppp) from ECG signal in which the funnel area of the PPP exhibits an irregular and highly complex pattern, indicative of ventricular fibrillation. The main objective of U.S. Pat. No. 5,643,325 is to determine that when a normal patient have a PPP which exhibits the regularity and smoothness of an ECG signal from that normal patient, while a patient undergoing VF will have a PPP which exhibits the irregularity and complexity of an ECG signal which might be deterministic chaos (e.g., a periodicity, banding and "forbidden zones"). When a patient in transition from normal into VF (i.e., in VF onset) exhibits a PPP which is consistent with an assessment that the ECG signal for the patient is in transition to deterministic chaos. One of major drawback of this conventional technique is that the analyzing and processing are labor intensive in which the data have to be analyzed and calculated through a complex method, and it is suit for ventricular fibrillation analysis only. In other words, this conventional technique is difficult and time-consuming to process and assess all the data.

SUMMARY OF INVENTION

The present invention provides a rapid method for analyzing bio-signal by CPSD and the measurement and analysis device. The object is to overcome the defects of the bio-analysis method described in the prior art for consuming more system resources and wasting much time on determination for not achieving instantaneous analysis. The CPSD analysis method employed by the present invention is based on the following steps to proceed the bio-signal analysis:

1. With the following steps to establish the phase space matrix:

A. abstracting the bio-signal, and after filtering out the unnecessary noise by the filter, selecting the suitable normalization factor and applying the normalization on the amplitude; and, employing the normalization factor to define the size of the rebuilt multi-dimensional phase space matrix, and initializing the phase space matrix to configure the initial value as zero;

B. on the signal time axis, selecting the original as the datum point, and selecting the suitable time interval from the datum point as the reference point;

C. employing the bio-signal strength at the datum point and reference point as the two coordinates of the phase space matrix, and accumulating the values at the corresponding location of the phase space matrix;

D. sequentially increasing the datum point and the reference point; repeating Step C until all the bio signals are processed.

2. With the following steps to rebuild the phase space matrix to obtain the chaotic phase space difference:

A. selecting suitable parameter configuration, including data length, time interval, sampling rate, size of phase space matrix, and normalization factor, and the like;

B. establishing the phase space matrix of reference bio-signal, which is referred as a reference matrix in brief;

C. establishing a phase space matrix for analyzing the bio-signal, which is referred as an analysis matrix in brief;

D. establishing a phase space matrix for storing the bio-signal, which is referred as a result matrix in brief;

E. calculating the variance of the label points of two space matrixes, and the calculation employs the analysis matrix shown in Step C and the reference matrix shown in Step B; because the sized of the two matrixes are the same, they could be directly conducted with subtraction operation; and, the operation will subtract the values of matrix elements in the analysis matrix from the values of matrix elements with the same coordinates in the reference matrix; and, the subtraction result is stored in the same coordinate positions in the result matrix; and, after completion of subtracting each coordinate element in the matrix, counting the data with the non-zero value in the result matrix, and the counted data is the chaotic phase space difference (CPSD value); and, employing the mean of CPSD values and the variance of standard deviation, which could automatically suitably adjust the threshold and the scope thereof, and the calculation is the mean plus/minus three times of standard deviation (SD).

3. Differentiating normal and abnormal ECG signal:

Based on the chaotic phase space difference algorithm, it will select the suitable threshold range as the basis of differentiation. When the CPSD value exceeds the scope, it will be determined as an abnormal ECG signal, as shown in FIG. 3A. The curve A (solid circle) indicates the variance curve for CPSD value obtained by the calculation with CPSD algorithm; the curve B (phantom circle) and the curve C (solid inversed triangle) indicate the upper limit (mean+3*SD) and the lower limit (mean−3*SD) of the threshold scope, respectively. When the CPSD value is within the threshold range, the ECG signal establishing the phase space matrix will be determined as normal. When the CPSD exceeds or is lower than the threshold range, the ECG signal establishing the phase space matrix will be determined as abnormal. As shown in FIG. 3B, the solid line indicates the ECG signal abstracted and loaded for analysis; the phantom line indicates the analyzed result, and the zero and non-zero value indicated the normal and abnormal ECG signal, respectively. For example, the highest value 400 in FIG. 3B indicates the abnormal ECG signal. It could be found that the ECG signal could be differentiated with the abnormal portion of the premature ventricle contraction by successfully and completely labeled by the CPSD analysis method.

4. Determining if the heart sound signal has occurred murmur:

Employing the CPSD value to calculate the mean and standard deviation (SD) of CPSD value in fixed length, as shown in FIG. 3C; the solid line indicates the CPSD value variance curve calculated with the CPSD algorithm, and the thin phantom line and the thick phantom line indicate the mean and the SD, respectively; when there is not murmur in the heart sound signal, the SD will be larger than the mean; when the murmur is appeared, as shown in FIG. 3D, the mean will be larger than the SD; and, it could be found that the central noise portion of the heart sound signal could be successfully and completely distinguished with the CPSD analysis method.

5. Determining the speed variation in respiration signal:

The CPSD value could be used to indicate the variance of the respiration speed. As shown in FIG. 3E, the phantom line indicates the CPSD value variance curve calculated with the CPSD algorithm, and the solid line indicates the respiration signal, which could be found that when the difference of respiration speed becomes larger, the relative CPSD value will also be increased.

DETAILED DESCRIPTION OF PREFERRED EMBODIMENTS

In order for the examiners to understand the objects, the features and the effects of the present invention, the following embodiments associated with the attached figures will be described in details for the present invention as follows. The present embodiment employs the ECG signal analysis as an example, but the same analysis model could be applied to the bio-signal with periodical variance. Further, the method of present invention is not intend to be restricted applying to a specific type of device or in the medical field. Other activities such as in the electrical field can employ this method to determine and analyze the normal and abnormal signals.

Figure 6:
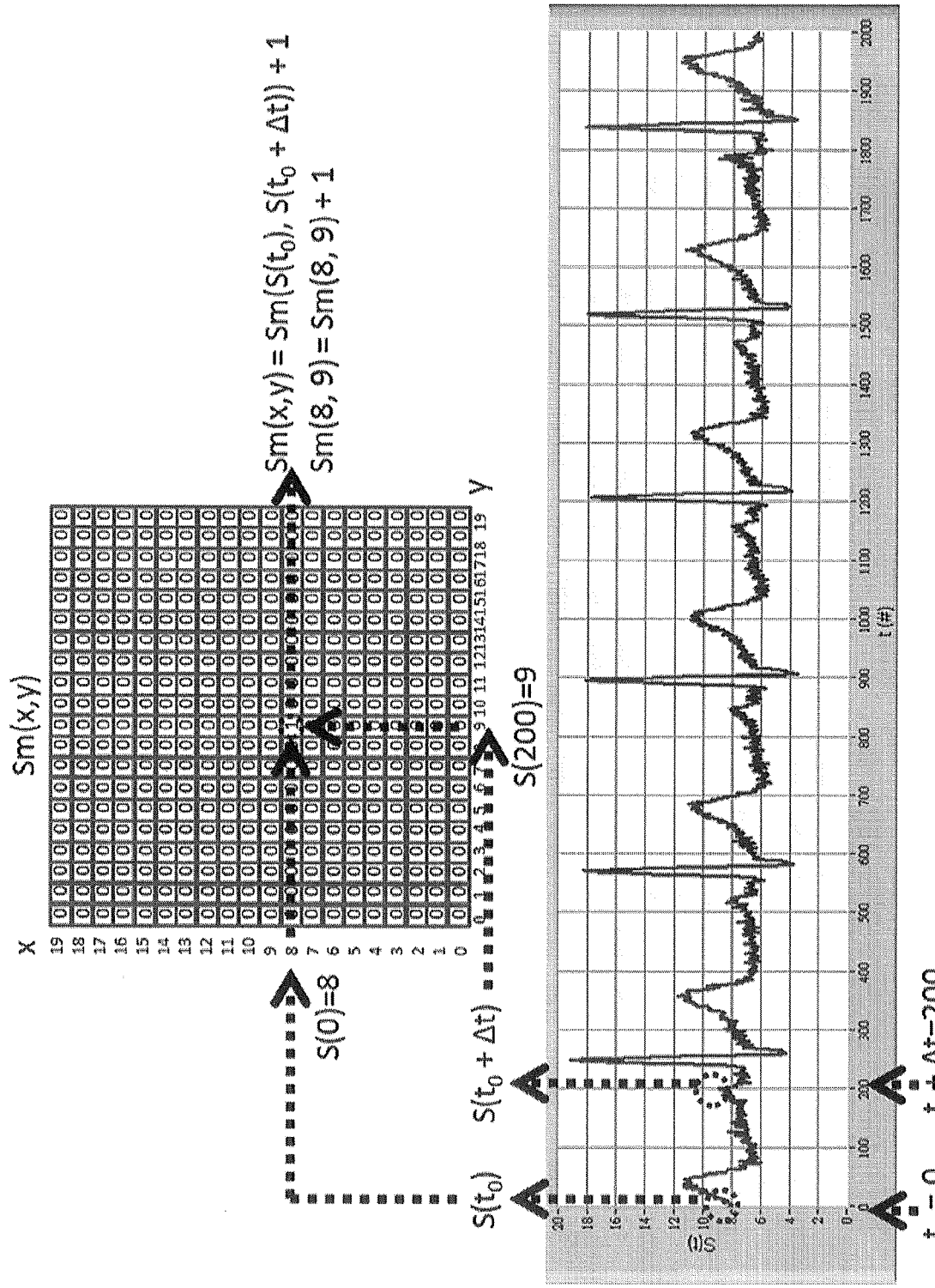
FIG. 6 is Flow chart of embodiment for calculating CPSD value.

1. Flow chart of embodiment for calculating CPSD value:

Employing the ECG signal abstraction device to abstract the ECG signal with the preferred sampling rate at 250~500 Hz; the signal obtained after abstraction will be with suitable data length to establish the phase space matrix with the preferred data length as 5~10 seconds; this section of flow for establishing the phase space matrix using ECG signal is shown in FIG. 6 for the initialization portion of the phase space matrix, the size of the matrix is the same as the normalization factor of the ECG. The size of phase matrix in FIG. 6 is 20×20, so the maximum value of ECG signal after amplitude normalization is 20 with the preferred normalization parameter is 20~50, and the initial values for the elements in the phase space matrix after initialization is configured as zero; next, employing the ECG signal after normalization to establish the phase space matrix, which the datum point is started from the original of the time coordinate; then, obtaining the coordinates of reference points after selecting suitable time interval with the preferred time interval at 0.2~1 seconds. To grain a value of the phase space matrix, step 1, when $t_0$ is set as 0 and $\Delta t$ is set as 200, a set of coordinate of the phase space matrix is obtained as $Sm(x,y)$, wherein the coordinate of the reference point is x=0-19, and y=0-19 so as to obtain a set of coordinates (0-19, 0-19). Step 2 to obtain a corresponding signal strength from ECG at the coordinate $t_0$ and $t_0+\Delta t$ is $S(t_0)$ and $S(t_0+\Delta t)$. Step 3, When $x=S(t_0)$ and $y=S(t_0+\Delta t)$, one is added to the contents of element labeled with coordinates $Sm(x,y)$ in the phase space matrix. Therefore, when the value of $\Delta t$ is fixed, one is added to the value of $t_0$ and the process is repeated through step 2-step 4 until $t_0$=length of ECG–$\Delta t$.

Figure 7:
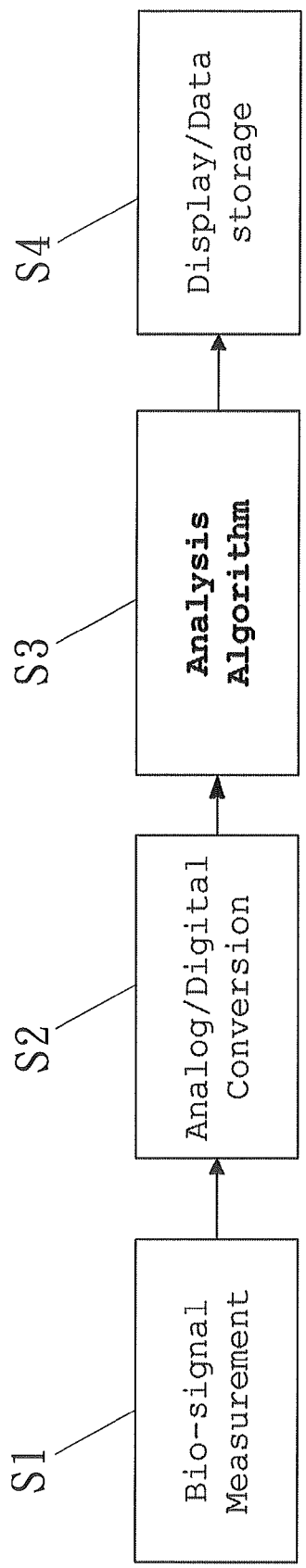
FIG. 7 is a block diagram for analyzing Bio-signal with CPSD algorithm.

FIG. 7 illustrates the steps of the method of present invention to analyze the Bio-signal with CPSD algorithm: S1—receiving the bio-signal measurement from the device; S2—conversing analogically and digitally the data; S3—analyzing the algorithm; and S4—displaying and storing the obtained data.

Figure 5A:
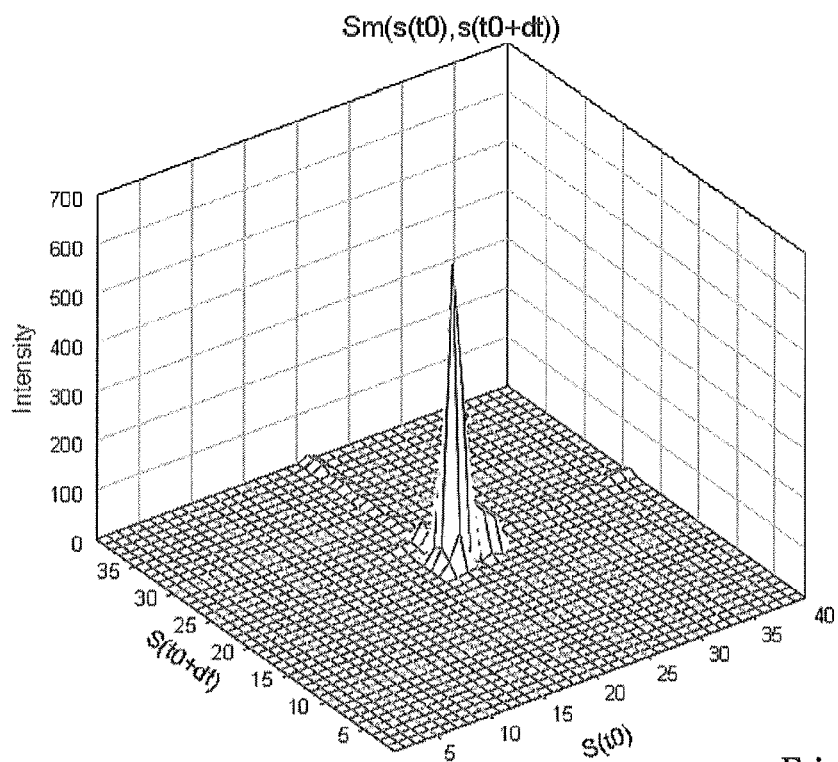
FIG. 5A is a reference matrix established with the normal ECG signal.
Figure 5B:
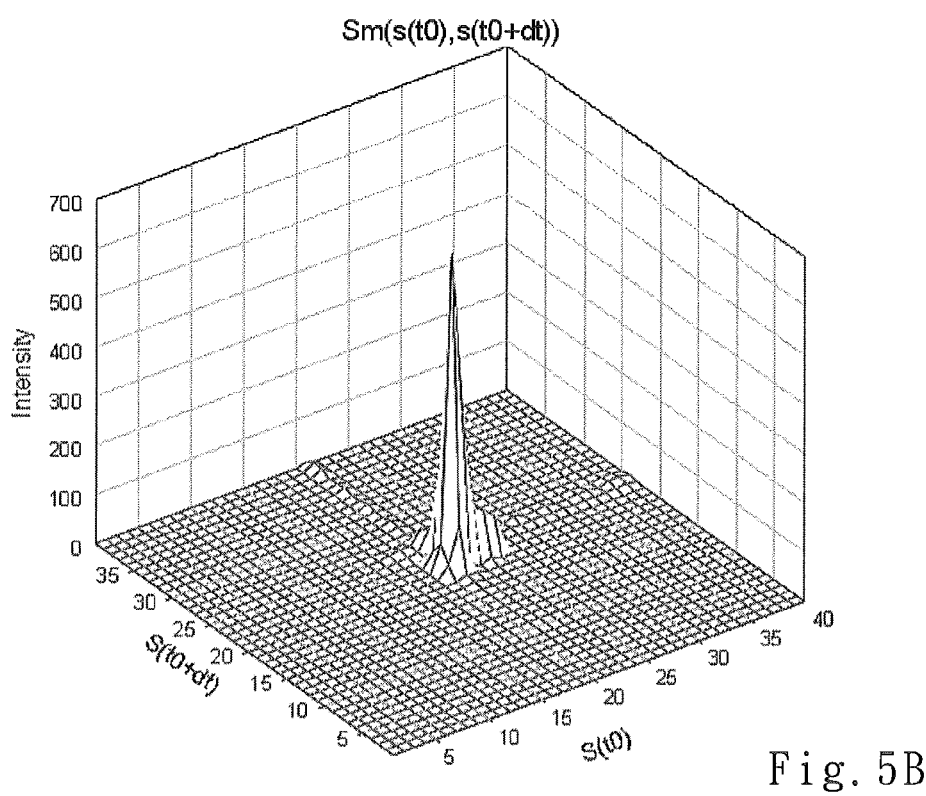
FIG. 5B is an analysis matrix established with the normal ECG signal.
Figure 5C:
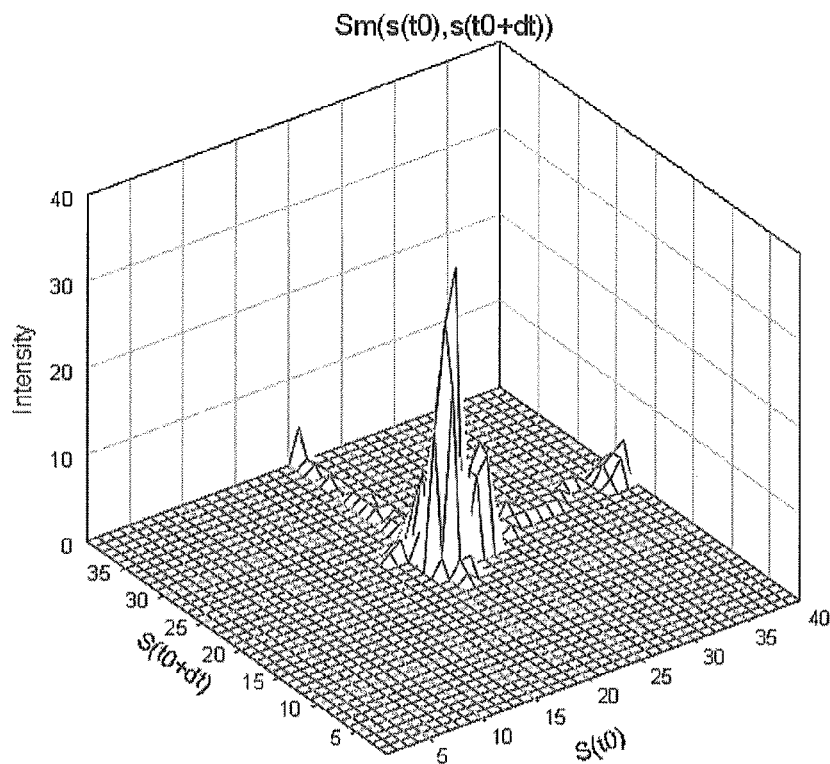
FIG. 5C is a computed result matrix with the normal ECG signal.
Figure 5D:
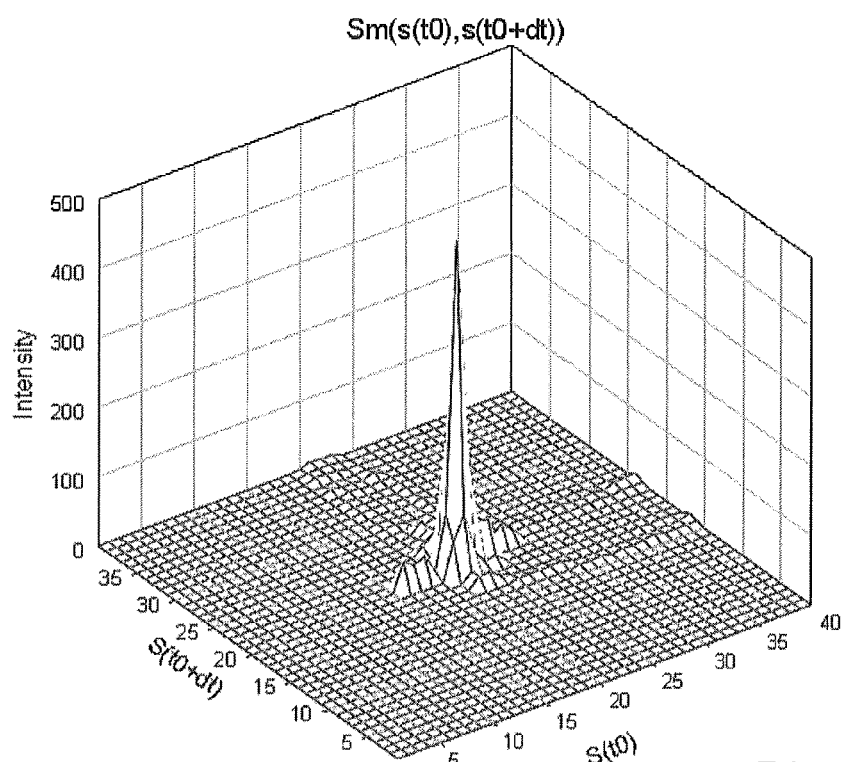
FIG. 5D is a reference matrix established with the abnormal ECG signal.
Figure 5E:
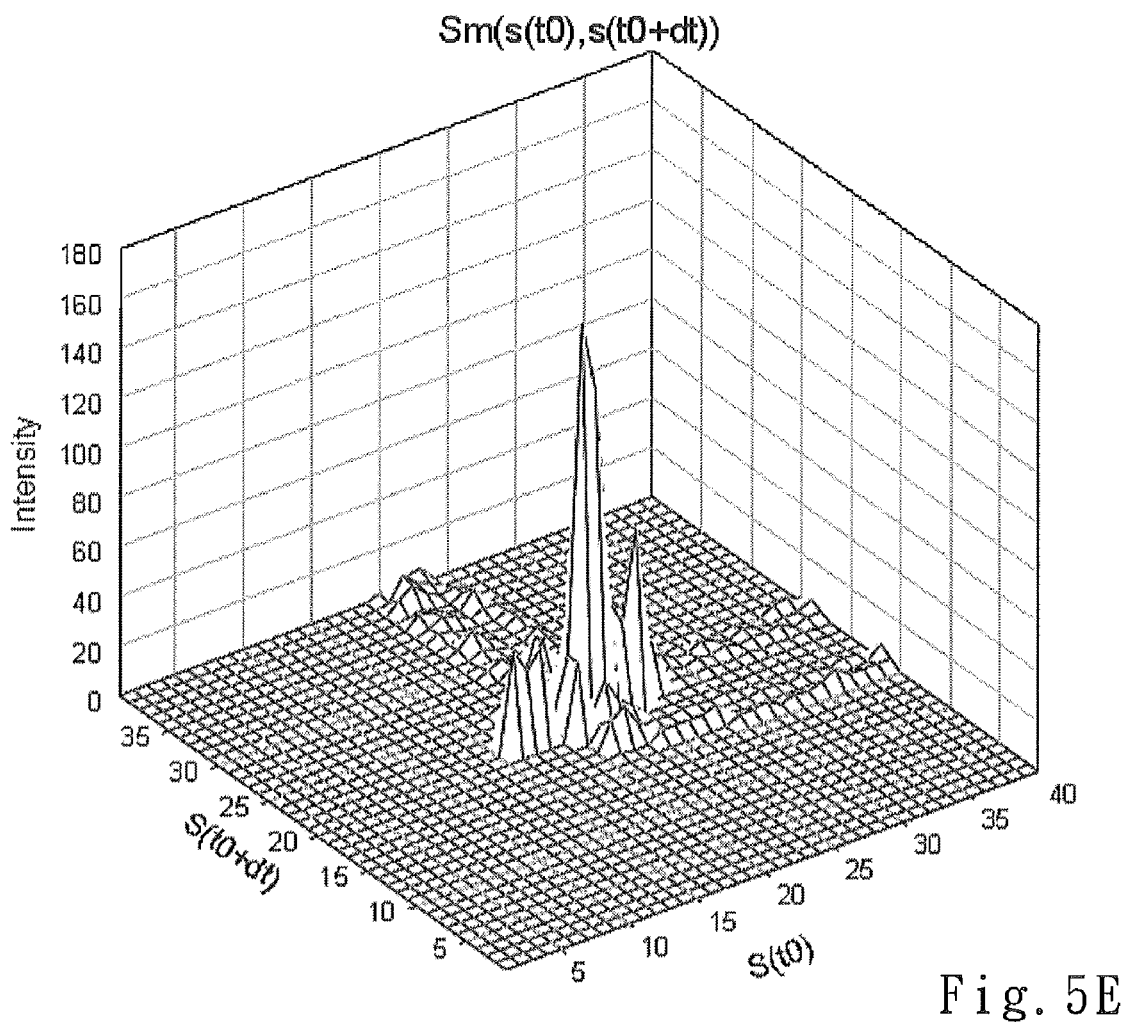
FIG. 5E is a computed result matrix with the abnormal ECG signal.

FIG. 5A is the reference matrixes representing normal ECG signals; FIGS. 5B and 5C are the analysis matrixes representing normal and abnormal ECG signals respectively. FIGS. 5D and 5E are the result matrixes representing normal and abnormal ECG signals respectively.

By subtracting the contents of the analysis matrix from the contents of the reference matrix, the difference between two matrixes could be obtained, and the subtraction result is stored in the result matrix. From FIG. 5A shows that the reference of the phase space matrix, wherein FIG. 5F indicates a normal state of the ECG signal and FIG. 5.B indicates the generated phase space matrix as an analysis matrix of normal case. FIG. 5C represents the results matrix of difference between matrixes of FIG. 5B and FIG. 5A through subtraction calculation. From the result, the complexity of two generated phase space matrixes is very similar, and through subtraction calculation, the result shows that degree of chaos is reduced. FIG. 5G indicates an abnormal state of the ECG signal and FIG. 5.D indicates the generated phase space matrix as an analysis matrix of abnormal case. FIG. 5E represents the results matrix of difference between matrixes of FIG. 5D and FIG. 5A through subtraction calculation. From the result, the complexity of two generated phase space matrixes is different, and through subtraction calculation, the result shows that degree of chaos is increased. In this algorithm, the calculation result by counting the number of data with non-zero value in the result matrix is the CPSD value.

Figure 1:
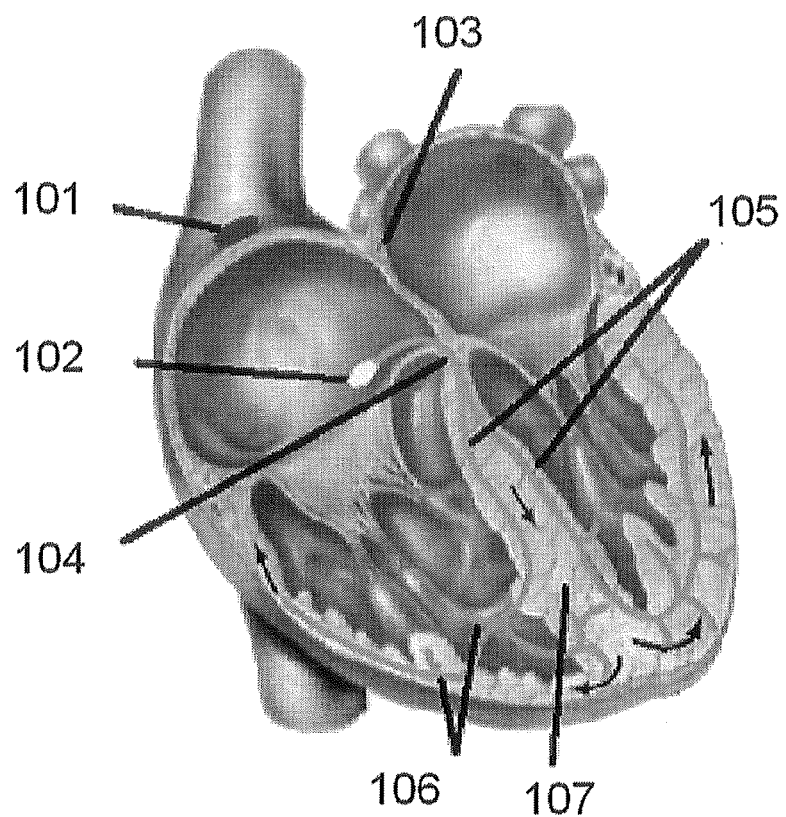
FIG. 1 is a cross-sectional diagram of heart structure.
Figure 2A:
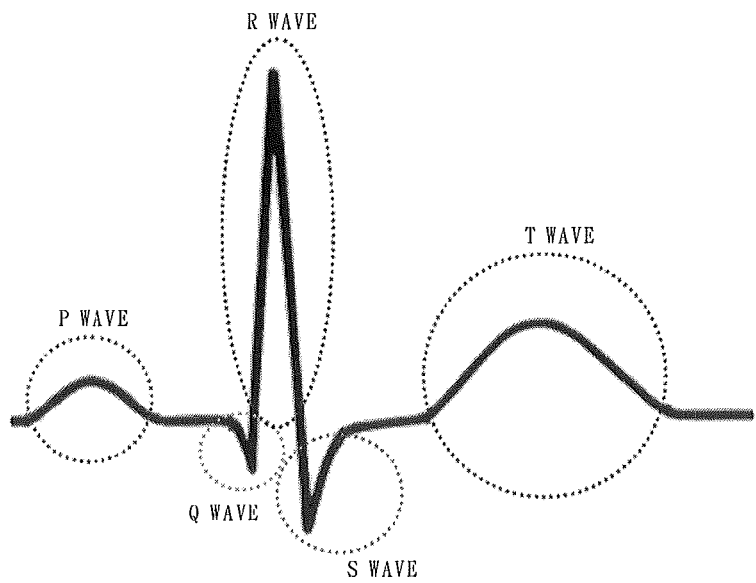
FIG. 2A is an ECG signal cycle recorded by the body surface electrode.
Figure 2B:
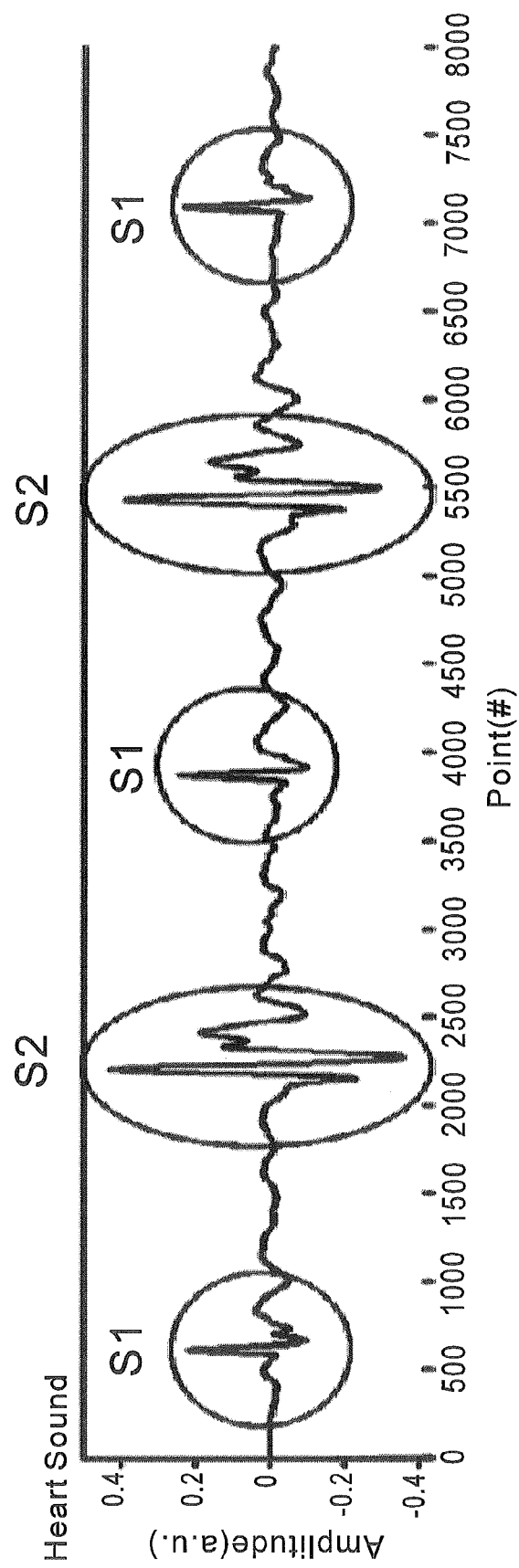
FIG. 2B is the normal heart sound signal.
Figure 2C:
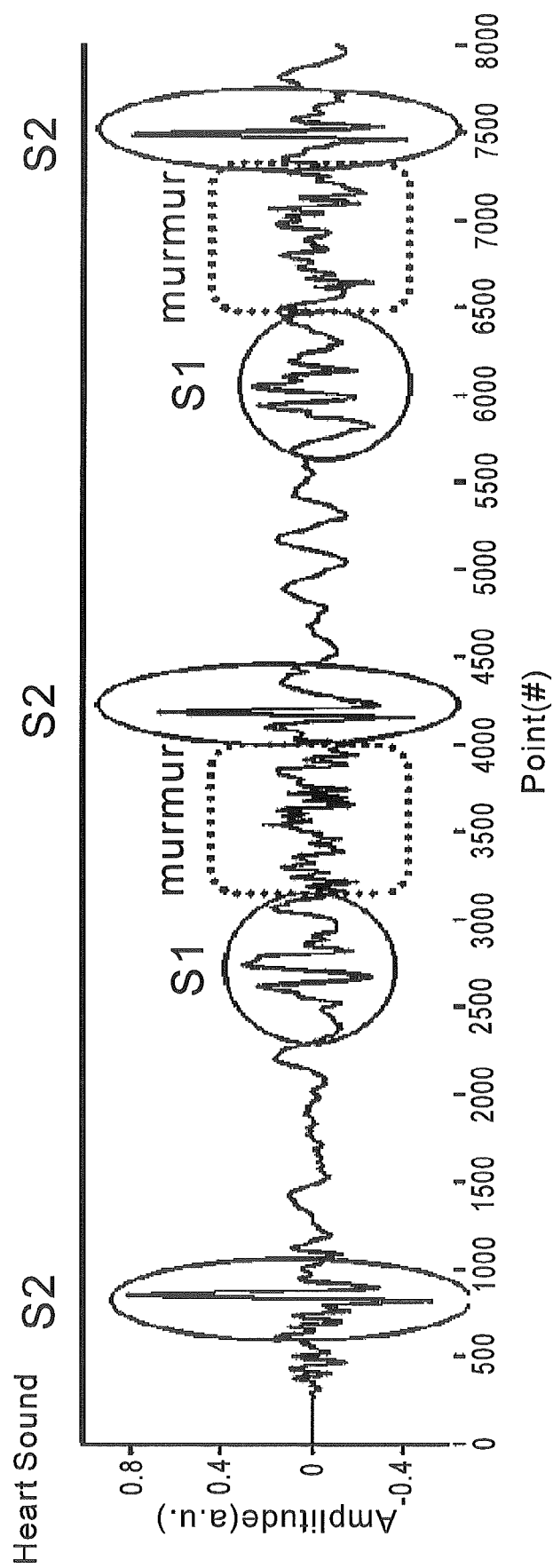
FIG. 2C is the heart sound signal with murmur.
Figure 2D:
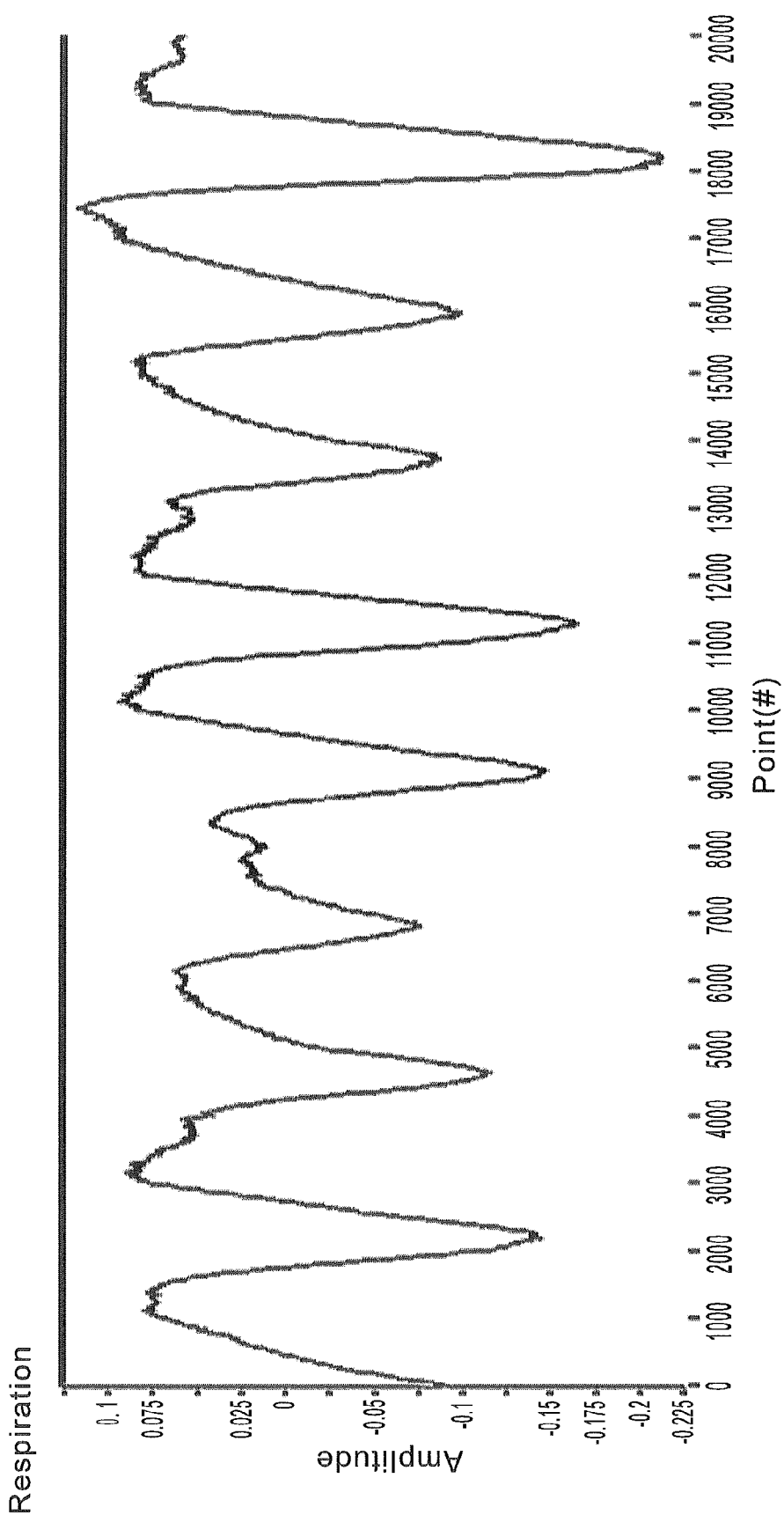
FIG. 2D is a respiration signal.
Figure 3A:
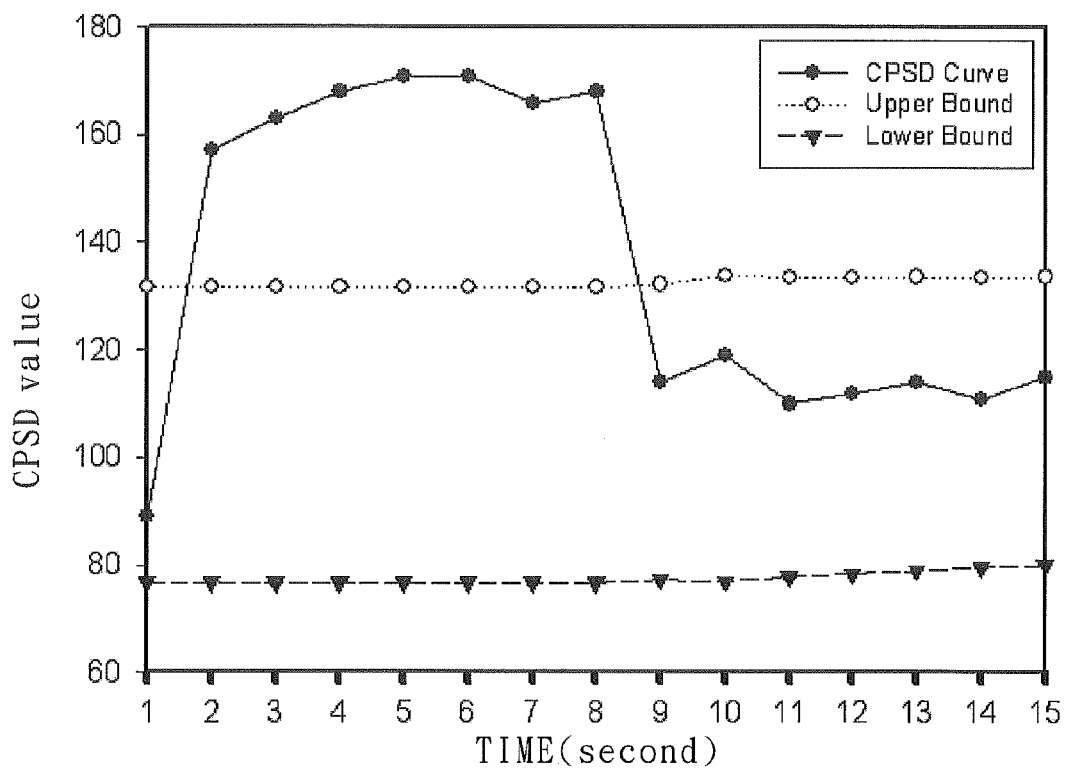
FIG. 3A is the determination of CPSD value signal between normal and abnormal ECG.
Figure 3B:
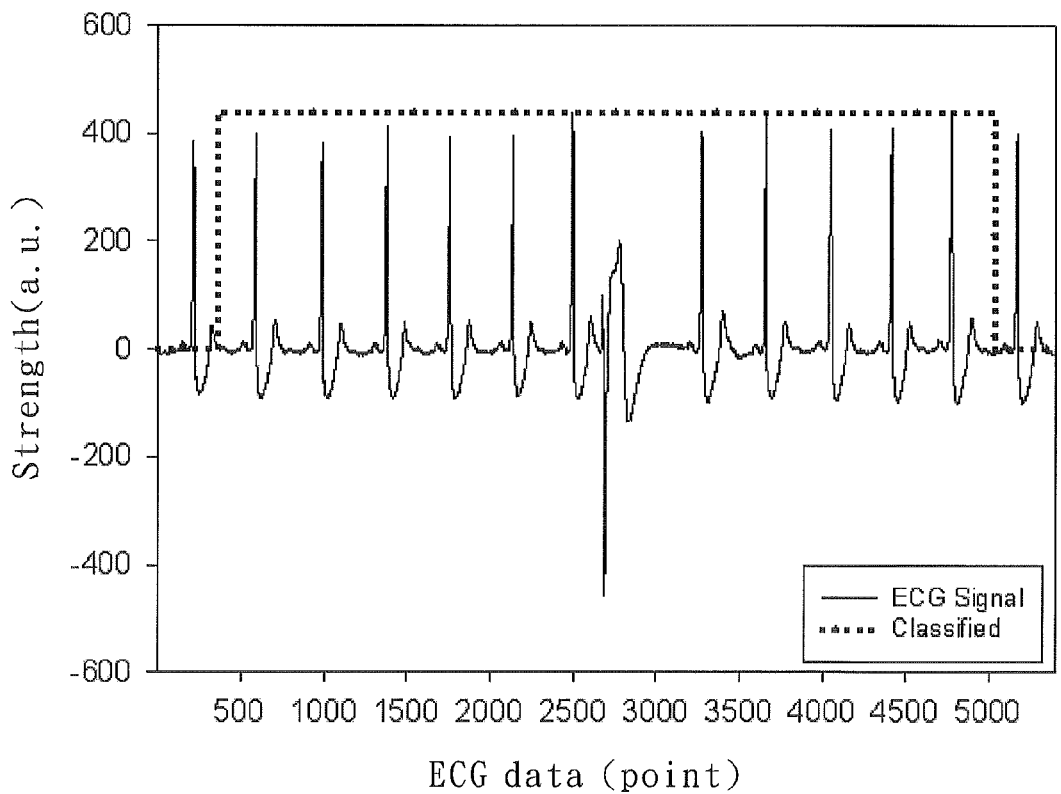
FIG. 3B is the normal and abnormal ECG signals.
Figure 3C:
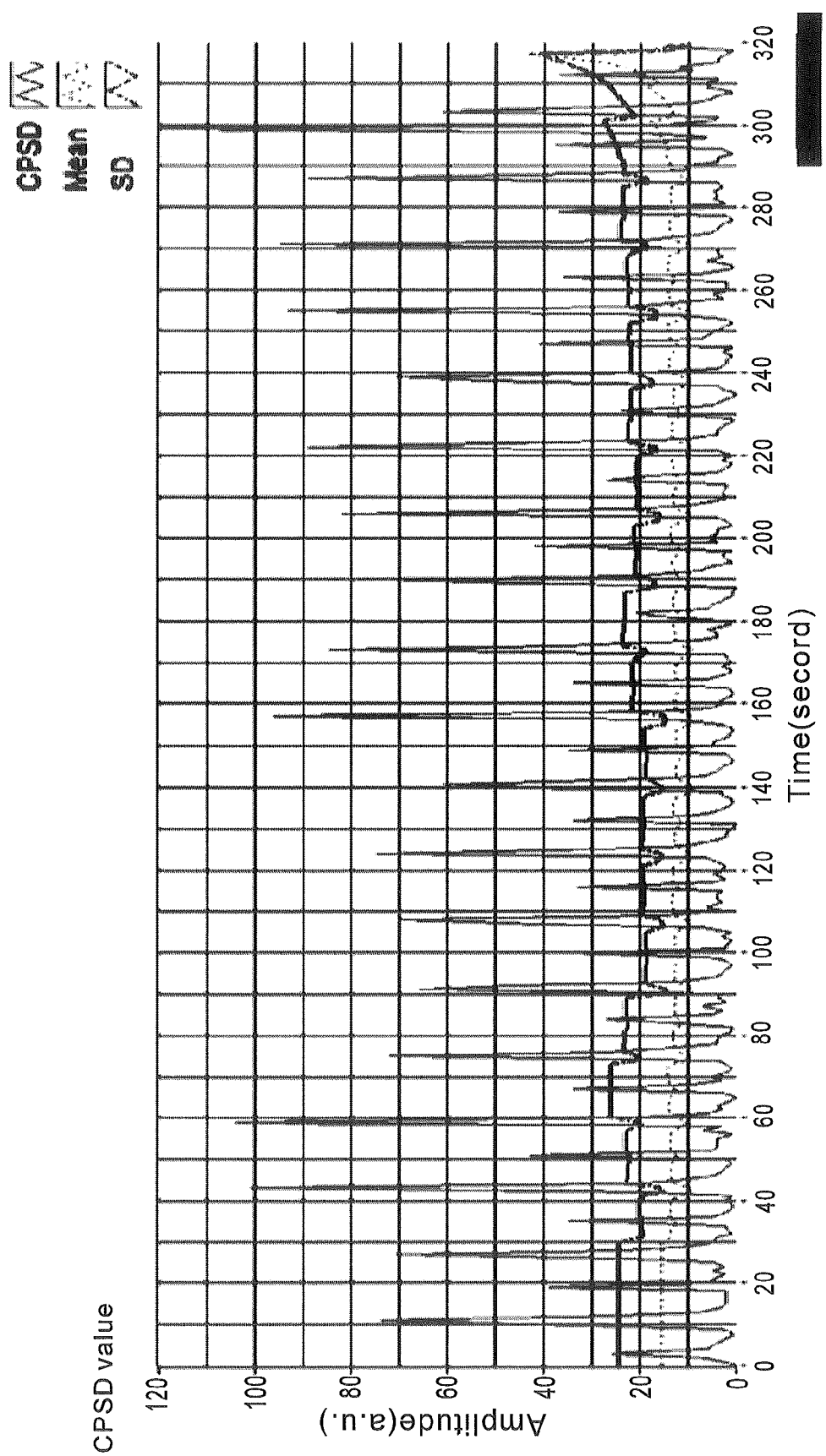
FIG. 3C is the CPSD value, the mean and the SD for normal heart sound signal.
Figure 3D:
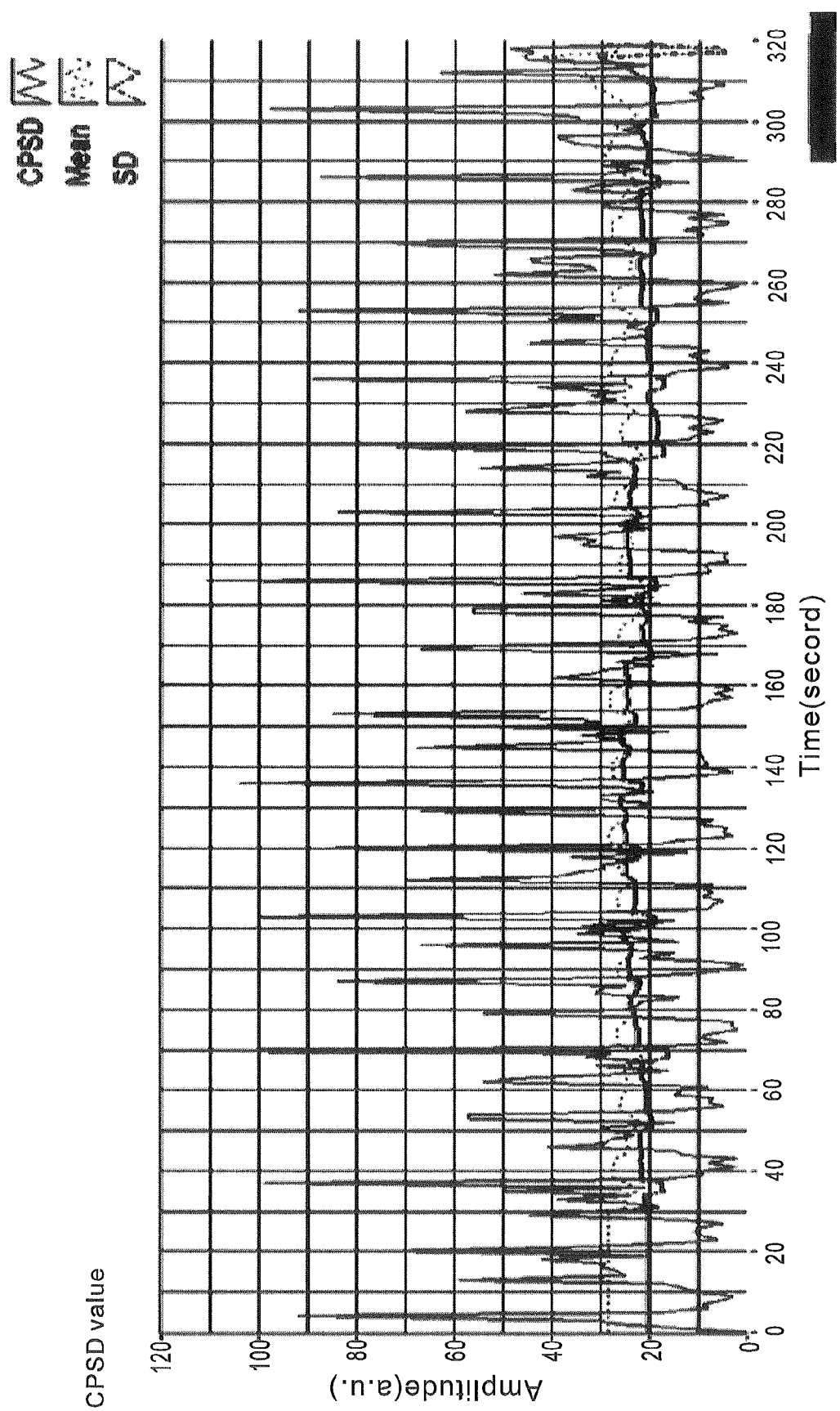
FIG. 3D is the CPSD value, the mean and the SD for murmur signal.
Figure 3E:
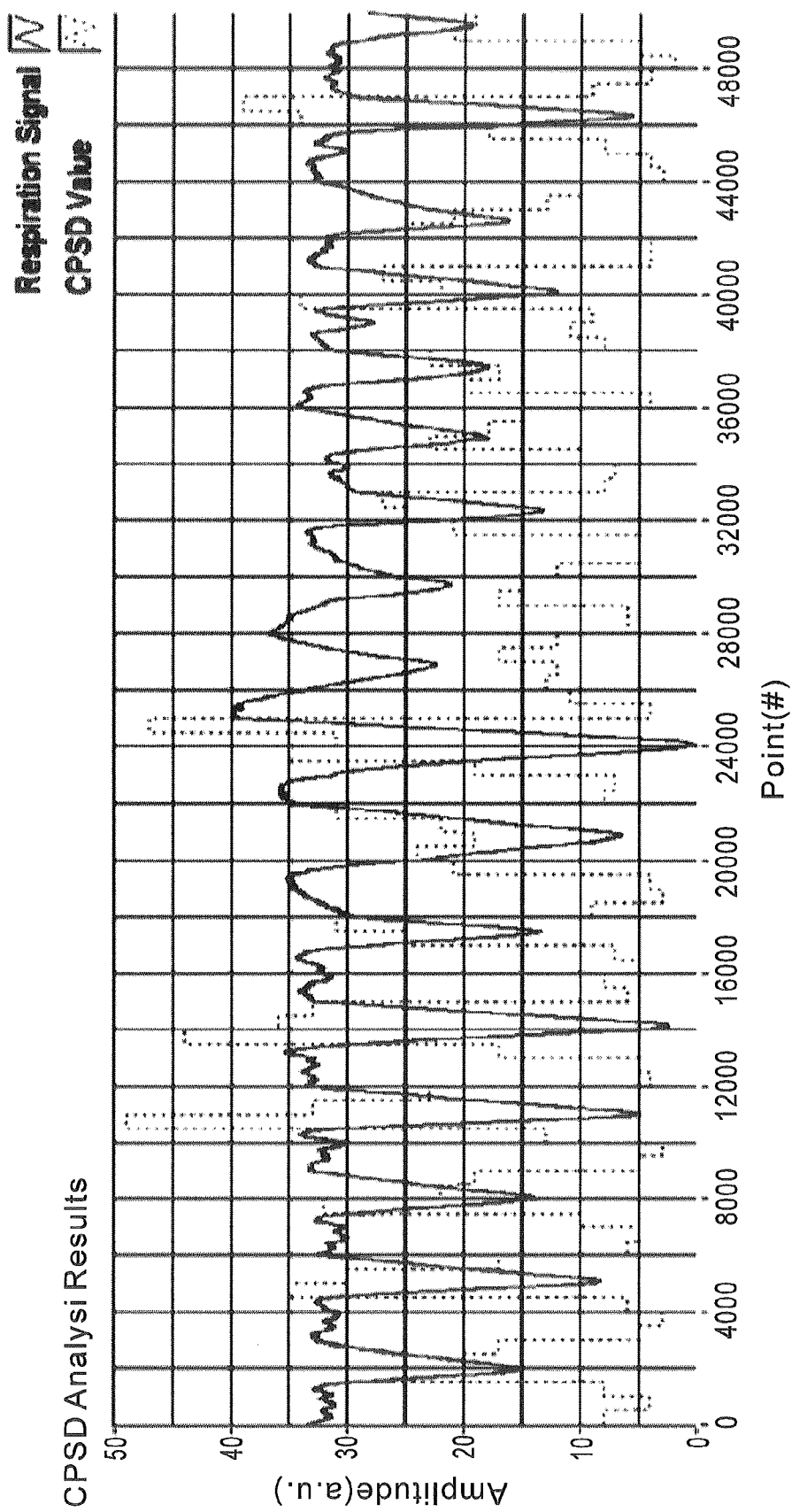
FIG. 3E is the respiration signal and the CPSD value curve.

2. Differentiating the normal and abnormal ECG signals:

Employing the CPSD, it could select the suitable threshold range as the basis for differentiation. When the CPSD exceeds the range, it would be determined as an abnormal ECG signal. As shown in FIG. 3A, the curve A indicates the variance curve of CPSD obtained using CPSD algorithm, and the curve B and the curve C indicate the upper limit and the lower limit of the threshold range, respectively. When the CPSD is within the threshold range, the ECG signal for establishing the phase space matrix at this time will be determined as normal. When the CPSD exceeds or is lower than the threshold range, the ECG signal for establishing the phase space matrix at this time will be determined as abnormal. As shown in FIG. 3B, the solid line indicates the ECG signal abstracted and loaded for analysis, and the phantom line indicates the analyzed result, and the zero and non-zero indicates the normal and abnormal ECG signal, respectively. For example, the highest value 400 in FIG. 3B indicates the abnormal ECG signal. It could be found that the ECG signal could be differentiated with the abnormal portion of the premature ventricle contraction (PVC) by successfully and completely labeled by the CPSD analysis method.

FIG. 3A shows the abnormal EFG signal (PVC), and FIG. 5D illustrates the constructed phase space matrix. FIG. 5E shows the result matrix of the difference between the matrixes of FIG. 5A and FIG. 5E by using the subtraction calculation. When abnormal ECG signal appears, the CPSD of the phase space matrix will vary, and through the subtraction calculation of the contents of the analysis matrix from the contents of the reference matrix, the result of differentiation of the two matrixes will indicate both the overlapping range of CPSD and the differentiation of the CPSD (variation range). Therefore, the efficiency of the calculation is drastically improved.

Figure 4:
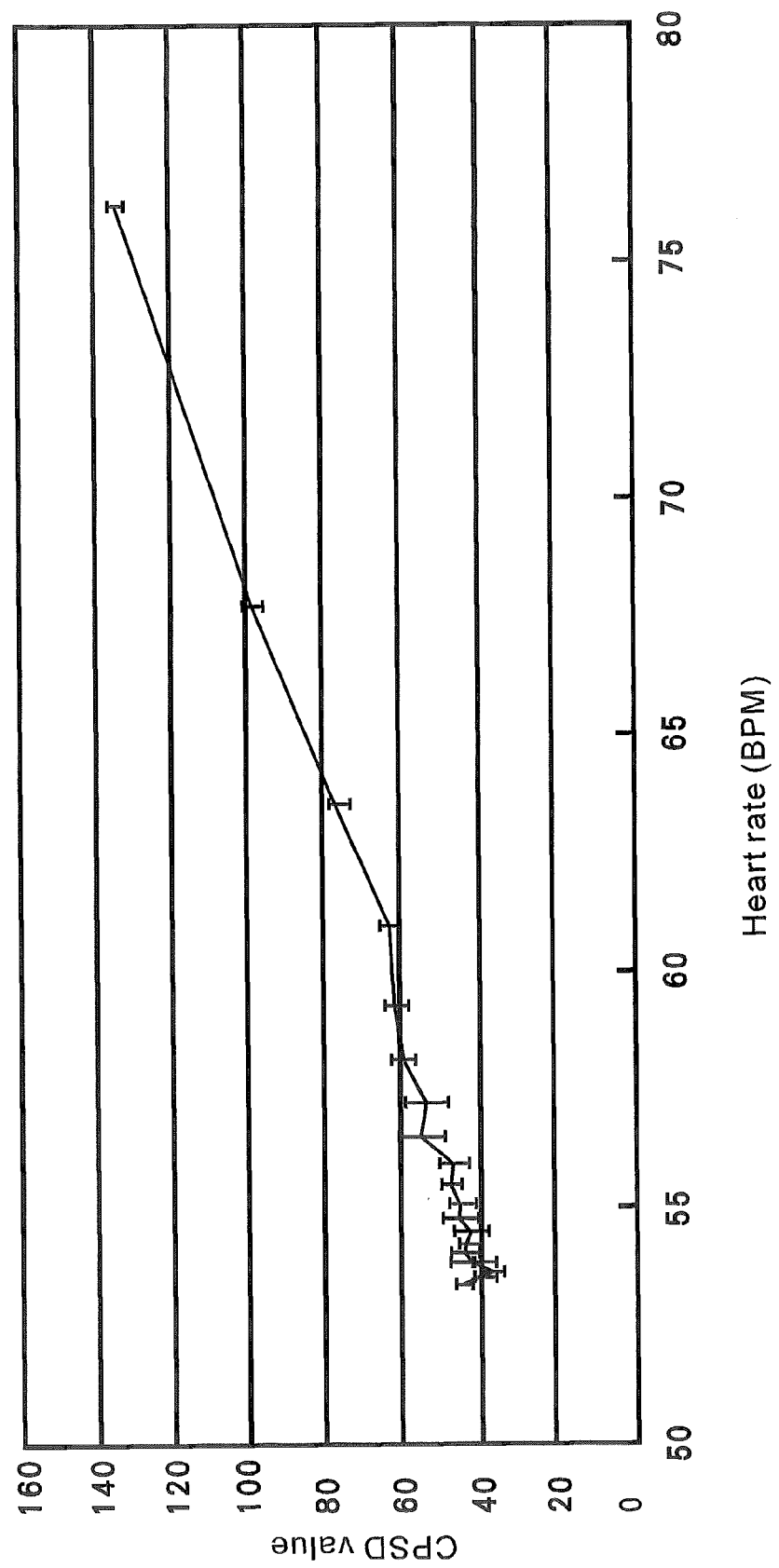
FIG. 4 is the relationship between heart rhythm and corresponding CPSD value.

3. Calculating the heart rate of normal ECG signal:

In the CPSD analysis method, when CPSD is located within the threshold range, CPSD could be used to calculate the corresponding heart rate. The relationship between heart rate and CPSD shown in FIG. 4 could be found that when the heart rate is larger than 62 bpm (bit per-minute), the heart rate and the CPSD will exhibit with a very good linear relationship. Moreover, the variation range (standard deviation) for CPSD will not have overlapped effect. Thus, the CPSD could be used to calculate the corresponding heart rate as the reference for other determination.

The method of the present invention can be utilized in any field and any kind of mechanism that detecting periodical signals. Thus, the method of the present invention is not limited or restricted in the medical field or electrocardiogram area.

4. ECG signal analysis result in arrhythmia database (BIH-MIT):

The table below represents the ECG signals for different diseases in BIH-MIT based on the determination result using PSD analysis method, and each data length is for 30 minutes, and the sampling rate is 360 Hz; wherein, V indicates the Premature Ventricular Contract, A indicates the Atrial premature contraction, a indicates the aberrated atrial premature, F indicates the Ventricular fusion beat, and VT indicates the Ventricular Tachycardia.

| Database Record | Used/Total Memory Space | catched | loosed | Sensitivity | Hint |
|---|---|---|---|---|---|
| 101 | 0.09 | 4 | 5 | 0.44 | A |
| 103 | 0.38 | 2 | 0 | 1.00 | A |
| 106 | 0.53 | 513 | 7 | 0.99 | V |
| 113 | 0.10 | 5 | 1 | 0.83 | A |
| 116 | 0.69 | 108 | 2 | 0.98 | V, A |
| 123 | 0.10 | 3 | 0 | 1.00 | V |
| 205 | 0.38 | 85 | 0 | 1.00 | VT, V, F, A |

By embedding the CPSD analysis method into the microprocessor, it could be used for ECG analysis in the following devices:

(1) Standalone 24-hour ECG recorder;

(2) Portable apparatus for instantaneously measuring, analyzing and recording ECG signal, such as PDA and cell phone;

(3) Improvement on the performance of the existed ECG measurement and analysis device; and, (4) Integrated ECG measurement and analysis system composed by combining the transmission interface.

5. The preferred range and the optimized value for the parameters used in CPSD algorithm:

Using CPSD algorithm to analyze the bio-signal must be configured with the value range for associated parameters according to different bio-signal characteristics. Based on the result of experimental analysis, the preferred range and the optimized value for the associated parameters used in the related bio-signal analysis is provided for the reference in implementation.

a. ECG signal:
  i. Sampling rate: the preferred range is 250~500 Hz, and the optimized value is 360 Hz;
  ii. Data length: the preferred range is 5~10 seconds, and the optimized value is 7 seconds;
  iii. Normalization factor: the preferred range is 20~50, and the optimized value is 40;
  iv. Time interval: the preferred range is 0.2~1 seconds, and the optimized value is 0.2 seconds; and,
  v. Size of phase space matrix: the preferred range is 20~50, and the optimized value is 40.

b. Heart sound signal:
  i. Sampling rate: the preferred range is 5 k~10 kHz, and the optimized value is 8 kHz;
  ii. Data length: the preferred range is 10~50 ms, and the optimized value is 25 ms;
  iii. Normalization factor: the preferred range is 20~50, and the optimized value is 40;
  iv. Time interval: the preferred range is 1~2 ms, and the optimized value is 1.25 ms; and,
  v. Size of phase space matrix: the preferred range is 20~50, and the optimized value is 40.

c. Respiration signal:
  i. Sampling rate: the preferred range is 250~500 Hz, and the optimized value is 500 Hz;
  ii. Data length: the preferred range is 5~10 seconds, and the optimized value is 7 seconds;
  iii. Normalization factor: the preferred range is 20~50, and the optimized value is 40;
  iv. Time interval: the preferred range is 0.2~1 seconds, and the optimized value is 0.2 seconds; and,
  v. Size of phase space matrix: the preferred range is 20~50, and the optimized value is 40.

Figure 8:
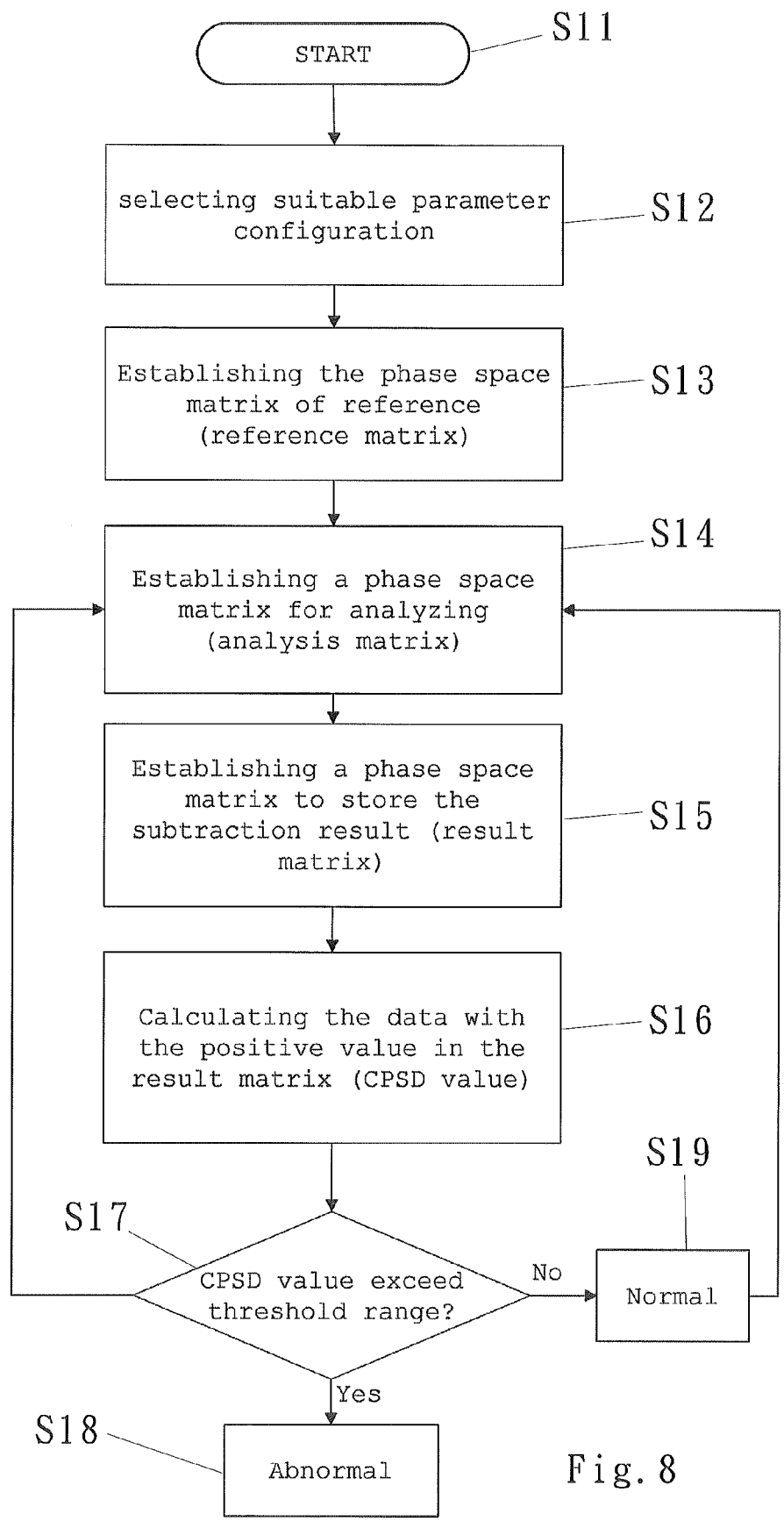
FIG. 8 is a flow diagram for establishing the phase space matrix.

FIG. 8 demonstrates how the method of analyzing of the present invention is operated.

S11—staring the electrical device;

S12—selecting a suitable parameter configuration, in which the parameter configuration can be pre-set;

S13—establishing a phase space matrix of reference (a reference matrix);

S14—establishing another phase space matrix for analyzing (an analysis matrix);

S15—establishing a phase space matrix to store the subtraction result (a result matrix) by employing the parameter of the size of the phase space in order to establish the result matrix;

S16—calculating the data with the non-zero value in the result matrix in order to obtain the CPSD value; S17—determining whether the CPSD value exceeds a pre-determined threshold range, if yes, the analyzing process goes to step S18, and if not, the analyzing process goes to step S19 or when the CPSD value cannot be determined for certain reasons, the analyzing process will return back to step S14. As mentioned-above, when the threshold range is determined, the normality of the CPSD value (ECG signal) can be established easily. FIGS. 3A & 3B illustrate that the curve A indicates the variance curve of CPSD values obtained using the CPSD algorithm, and the curve B and the curve C indicate the upper limit and the lower limit of the threshold range respectively. When the CPSD value is within the threshold range, the ECG signal for establishing the phase space matrix at this time will be determined as normal. When the CPSD value exceeds or is lower than the threshold range, the ECG signal for establishing the phase space matrix at this time will be determined as abnormal. As shown in FIG. 3B, the solid line indicates the ECG signal abstracted and loaded for analysis, and the phantom line indicates the analyzed result, and the zero and non-zero indicates the normal and abnormal ECG signal, respectively;

S18—concluding the CPSD value is abnormal when the CPSD value exceeds the threshold range;

S19—concluding the CPSD value is normal when the CPSD value does not exceed the threshold range, the process will then go to back to step 14 and repeat the rest of the analyzing process.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A rapid method for analyzing a bio-signal instantaneously by phase space difference, comprising the following steps:
   (A) selecting a suitable parameter configuration;
   (B) establishing a one phase space matrix for reference and another phase space matrix for analyzing the bio-signal, wherein establishing the one phase space matrix for reference and analyzing phase space matrices includes:
     (a) eliminating a noise interference in the bio-signal,
     (b) employing a parameter of a size of the phase space matrix as a basis of a normalization factor,
     (c) conducting a normalization process on an amplitude of the bio-signal,
     (d) employing the normalization factor to configure the size of the phase space matrix, and initializing the contents in the phase space matrix as zero,
     (e) configuring a plurality of origin coordinates as coordinates of a datum point,
     (f) employing the parameter of a time interval and the datum point to configure the coordinates of a reference point,
     (g) employing a strength of the bio-signal at the datum point and the reference point to label the two coordinates of the phase space matrix, and adding the values in a location of the coordinates, and
     (h) sequentially adding the datum point and the reference point to establish the phase space matrix;
   (C) calculating a variance condition for the label points between the two space matrices to obtain a variance of a chaotic phase space difference; and
   (D) evaluating whether the chaotic phase space difference exceeds a threshold range, wherein when a complexity difference of the chaotic phase space difference exceeds the threshold range, the bio-signal is considered to be abnormal, and when the complexity difference of the chaotic phase space difference does not exceed the threshold range, the bio-signal is considered to be normal.

2. The method for analyzing bio-signal according to claim 1, wherein the parameters configured in Step (A) includes a data length, a time interval, and a sampling rate.

3. The method for analyzing bio-signal according to claim 1, wherein the bio-signal is an ECG signal, a heart sound signal, a respiration signal, or other bio-signals with a periodic characteristic.

4. A rapid method for analyzing a bio-signal instantaneously by a phase space difference, comprising:
   (A) selecting a suitable parameter configuration;
   (B) establishing a one phase space matrix for reference and another phase space matrix for analyzing the bio-signal;
   (C) calculating a variance condition for a plurality of label points between the two space matrices to obtain a variance of a chaotic phase space difference, further comprising:
     (a) employing a method for establishing the phase space matrix and a reference bio-signal to establish a reference matrix;
     (b) employing a method for establishing the phase space matrix and an analysis bio-signal to establish an analysis matrix;
     (c) employing a parameter of a size of the phase space to establish a result matrix;
     (d) employing a subtraction operation to calculate a difference between each element value in the analysis matrix and the reference matrix, and storing an operation result in the result matrix;

(e) counting a number of elements with positive value in the result matrix to determine the chaotic phase space difference; and D) evaluating whether the chaotic phase space difference exceeds a threshold range, wherein when a complexity difference of the chaotic phase space exceeds the threshold range, the bio-signal is considered to be abnormal, and when the complexity difference of the chaotic phase space does not exceed the threshold range, the bio-signal is considered to be normal.

5. A rapid method for analyzing a bio-signal instantaneously by a phase space difference, comprising:
  (A) selecting a suitable parameter configuration;
  (B) establishing a one phase space matrix for reference and another phase space matrix for analyzing the bio-signal;
  (C) calculating a variance condition for a plurality of label points between the two space matrixes to obtain the variance of a chaotic phase space difference; and
  (D) evaluating whether the chaotic phase space difference exceeds a threshold range, wherein when a complexity difference of the chaotic phase space difference exceeds the threshold range, the bio-signal is considered to be abnormal, and when the complexity difference of the chaotic phase space difference does not exceed the threshold range, the bio-signal is considered to be normal;
  wherein evaluating whether the chaotic phase space difference exceeds a threshold range includes:
    (a) applying a statistical analysis on a suitable data number of the chaotic phase space difference, and calculating a mean and a standard deviation;
    (b) employing the mean and the standard deviation to calculate the threshold range; and
    (c) configuring the threshold range as the means plus/minus three times of the standard deviation.

6. The method for analyzing bio-signal according to claim 3, wherein when the bio-signal is an ECG signal and a respiration signal, the optimized range for suitable parameter configuration in Step (A) includes the followings:
  (a) Data length: 5~10 seconds;
  (b) Time interval: 0.2~1 seconds;
  (c) Sampling rate: 250~500Hz;
  (d) Normalization factor: 20~50; and,
  (e) Size of phase space matrix: 20~50.

7. The method for analyzing bio-signal according to claim 3, wherein when the bio-signal is a heart sound signal, the optimized range for suitable parameter configuration in Step (A) includes the followings:
  (a) Data length: 10~50 ms;
  (b) Time interval: 1~2 ms;
  (c) Sampling rate: 5k~10kHz;
  (d) Normalization parameter: 20~50; and,
  (e) Size of phase space matrix: 20~50.

8. A bio-signal measurement and analysis instrument, which is characterized in that a device is employed the method for calculating the chaotic phase space difference according to claim 4 as the analysis method for bio-signal.

9. The bio-signal measurement and analysis instrument according to claim 8, wherein the bio-signal is an ECG signal, a heart sound signal, a respiration signal, or other bio-signals with periodicity.

10. The bio-signal measurement and analysis instrument according to claim 9, wherein the device is provided with an embedded module with function for calculating the chaotic phase space difference.

11. The bio-signal measurement and analysis instrument according to claim 9, wherein the device could be used for 24 hours in a standalone manner.

12. The bio-signal measurement and analysis instrument according to claim 9, wherein the device may be a portable apparatus for instantaneously measuring, analyzing and recording the bio-signal.

13. The bio-signal measurement and analysis instrument according to claim 9, wherein the device is an integrated bio-signal measurement and analysis system composed by combining a transmission interface.

* * * * *